US010857254B2

(12) United States Patent
Graupner et al.

(10) Patent No.: US 10,857,254 B2
(45) Date of Patent: Dec. 8, 2020

(54) PROTECTIVE PIPE FOR A UV TUBE, IN PARTICULAR A UV-C TUBE

(71) Applicant: sterilAir AG, Weinfelden (CH)

(72) Inventors: Martin Graupner, Guettingen (CH); Simon Schlegel, Bischofszell (CH)

(73) Assignee: sterilAir AG, Weinfelden (CH)

( * ) Notice: Subject to any disclaimer, the term of this patent is extended or adjusted under 35 U.S.C. 154(b) by 0 days.

(21) Appl. No.: 15/561,102

(22) PCT Filed: Apr. 7, 2016

(86) PCT No.: PCT/IB2016/051967
§ 371 (c)(1),
(2) Date: Sep. 25, 2017

(87) PCT Pub. No.: WO2016/162816
PCT Pub. Date: Oct. 13, 2016

(65) Prior Publication Data
US 2018/0117208 A1 May 3, 2018

(30) Foreign Application Priority Data

Apr. 9, 2015 (DE) .......................... 10 2015 105 362

(51) Int. Cl.
*A61L 9/20* (2006.01)
*H01J 61/34* (2006.01)
(Continued)

(52) U.S. Cl.
CPC ................... *A61L 9/20* (2013.01); *A61L 2/10* (2013.01); *F21V 7/005* (2013.01); *H01J 61/34* (2013.01); *H01J 61/50* (2013.01)

(58) Field of Classification Search
CPC ................. A61L 2/20; A61L 9/20; A61L 2/10
See application file for complete search history.

(56) References Cited

U.S. PATENT DOCUMENTS

| 4,048,537 A | 9/1977 | Blaisdell et al. |
| 6,186,649 B1 * | 2/2001 | Zou .......................... F21V 7/005 |
| | | 362/217.05 |

(Continued)

FOREIGN PATENT DOCUMENTS

| DE | 699 12 253 T2 | 8/2004 |
| DE | 203 06 737 U1 | 9/2004 |

(Continued)

OTHER PUBLICATIONS

International Search Report of PCT/IB2016/051967, dated Jul. 13, 2016.

*Primary Examiner* — Donald R Spamer
(74) *Attorney, Agent, or Firm* — Collard & Roe, P.C.

(57) ABSTRACT

A protective pipe for a UV lamp for accommodating a tube includes a rod-shaped encasing pipe, wherein a viewing window is provided on the circumferential surface, through which viewing window the radiation, in particular the UV-C radiation, emitted by the tube can escape. A coating made of polytetrafluoroethylene is applied to the inner face of the protective pipe as a reflector. The protective pipe is composed of metal and is surrounded, at least in the region of the viewing window, by an at least partially transparent hose composed of plastic. Preferably, a transparent Teflon material is proposed for the hose.

3 Claims, 3 Drawing Sheets

Figure 1:
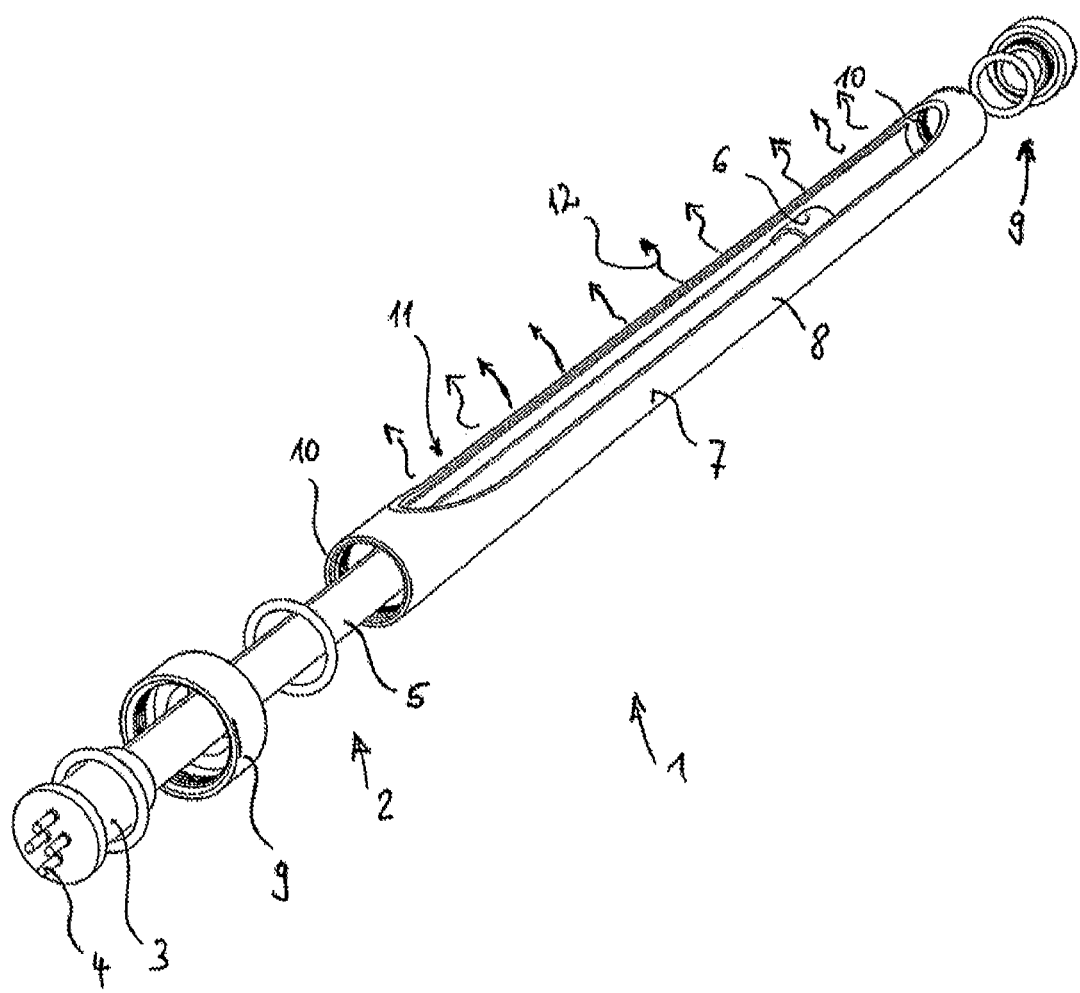

(51) Int. Cl.
*A61L 2/10* (2006.01)
*F21V 7/00* (2006.01)
*H01J 61/50* (2006.01)

(56) References Cited

U.S. PATENT DOCUMENTS

| | | |
|---|---|---|
| 6,397,839 B1 | 6/2002 | Stradella |
| 2006/0113485 A1 | 6/2006 | Ferres et al. |
| 2008/0048541 A1* | 2/2008 | Sumrall .................. H01J 61/52 |
| | | 313/112 |
| 2011/0002058 A1* | 1/2011 | Leonhardt ................ F26B 3/28 |
| | | 359/869 |

FOREIGN PATENT DOCUMENTS

| | | |
|---|---|---|
| JP | 2002-237209 A | 8/2002 |
| WO | 00/01986 A1 | 1/2001 |

\* cited by examiner

PROTECTIVE PIPE FOR A UV TUBE, IN PARTICULAR A UV-C TUBE

CROSS REFERENCE TO RELATED APPLICATIONS

This application is the National Stage of PCT/IB2016/051967 filed on Apr. 7, 2016, which claims priority under 35 U.S.C. § 119 of German Application No. 102015105362.4 filed on Apr. 9, 2015, the disclosure of which is incorporated by reference. The international application under PCT article 21(2) was not published in English.

TECHNICAL FIELD

The invention relates to a protective pipe for a UV lamp for accommodation of a tube having a rod-shaped encasing pipe, wherein a viewing window is provided on the circumferential surface, through which viewing window the radiation, particularly UV-C radiation, emitted by the tube can exit. Furthermore, it relates to the use of polytetrafluoroethylene for a UV lamp.

DEFINITIONS

UV means ultraviolet with reference to this application, and is used for characterization of a defined wavelength range.

Ultraviolet rays form part of the natural sunlight spectrum. Short-wave ultraviolet rays belong to the group of optical rays. Nevertheless, they are invisible for the human eye. The UV rays from what is called the C band (therefore referred to as UV-C) have a strong germicidal effect around 260 nm (nanometers). The kill rate is subject to the dose/effect principle; for this reason, technical characteristic data regarding tube power and the irradiation period are decisive for functionally reliable UV-C sterilization.

The germicidal effect acts, in particular, on bacteria, viruses, yeasts and molds. These microorganisms are effectively inactivated by means of what is called UV disinfection of air, water or surfaces. The technology of UV sterilization does not utilize any chemistry and no toxic compounds, and does not lead to mutation-related resistance formation. The undesirable microorganisms become inactive within seconds, while the product properties of the irradiated product remain almost unchanged. UV sterilization is particularly used in the sectors in which great demands exist with regard to consumer protection and requirements based on the HACCP concept.

Ultraviolet radiation is very energy-rich and triggers photochemical reactions in the respective nucleic acids of the exposed cell when the radiation is absorbed. If two thymines lie next to one another in the DNA strand, they react and form a dimer that is unusable for duplication and transcription. If multiple damage occurs, the cell is no longer able to regenerate. It loses the ability to divide and reproduce, and dies.

From economic aspects, germ reduction all the way to the 5-log stage is possible. The precise UV dose that leads to inactivation of the microorganisms differs by species, in this regard. While the predominant part of bacteria and viruses become inactive at a relatively slight dose, yeasts, molds, fungi, and spores require a correspondingly higher dose.

Short-wave UV-C radiation can be shielded against with usual window glass, transparent plastic, such as Makrolon® or acrylic glass, for example, as well as practically all non-transparent materials.

STATE OF THE ART

UV-C sterilization is particularly used in the foods-processing industry. Special demands are set for the UV-C source, on the basis of the environment in which the radiation sources are used. It must at least satisfy the IP52 standard.

The UV-C source is generally surrounded by an encasing pipe. This encasing pipe consists of a quartz glass that surrounds the radiation source. The encasing pipe with the UV source and the corresponding connectors forms the tube. If a UV-C source is provided, one also speaks of a UV-C tube. The electrical connectors, i.e. the connection from the UV-C source to a current connector, is formed by a socket that has corresponding electrical contacts, preferably pins. These are plugged into a holder, in the manner of a plug, in order to produce electrical contacts.

In order to protect the encasing pipe against breakage and to prevent splinters from being scattered in the event of breakage, it is provided that a protective pipe surrounds the encasing pipe. This protective pipe consist of a basic body composed of stainless steel or aluminum, preferably having rotation symmetry, and is dimensioned in such a manner that this basic body surrounds the encasing pipe at a distance.

Furthermore, a viewing window is provided on the circumferential surface, from which the radiation emitted by the radiation source exits. This viewing window is generally milled or lasered.

The inner wall of the protective pipe has a reflector, in such a manner that the radiation emitted passes through the viewing window at least in partially concentrated manner. This reflector generally consists of an aluminum layer or an aluminum alloy, such as aluminum/manganese, for example.

A highly efficient illumination source and a lighting system with an improved emitted radiation intensity is known from DE 699 12 253 T2. In the embodiments described, an elongated UV light source is proposed as a radiation source, which is surrounded by an extremely reflective casing. This casing is a plastic pipe that has an aperture opening. The size of this aperture opening is defined. In this regard, the casing is structured in such a manner that it is thin with regard to its wall, so that the radiation that is not reflected, and is converted to heat, can exit directly from the casing, because this has a negative influence on the power of the UV source.

Disadvantages of the State of the Art Part of the power of the UV-C tube is lost due to reflection of the UV radiation within the protective pipe. This means that little power is transported through the viewing window. For example, at a power of the tube of 58 W, an emitted UV-C irradiation intensity of approximately 14 mW/cm$^2$ is achieved at a distance of 2 cm relative to the opening window.

Aluminum or aluminum alloy has a degree of reflection of approximately 87-89%. As a result, the emitted power is low, and corresponding losses occur as a result.

However, aluminum can only be disposed in facet-like manner as a reflector; a surface that is round in cross-section and homogeneous is not formed. As a result, different reflection surfaces are obtained, which lead to different ray directions.

Task of the Invention

The task of the invention consists of increasing the emitted power of the UV-C tube, without changing the tube or the UV source and without losing the advantages of the protective pipe.

Solution of the Task

The first part of the basic idea of the solution consists in using a material that demonstrates better reflection in comparison with aluminum or the aluminum alloy, in order to thereby increase the emitted power from the viewing window.

The solution consists in using polytetrafluoroethylene (abbreviated PTFE, occasionally also polytetrafluoroethane), as the reflector material. Colloquially, this plastic is often identified with the trade name Teflon®.

In this way, great power constancy of the UV source is achieved.

A surrounding transparent hose also protects the encasing pipe, which would be freely accessible through the viewing window as such. The transmission capacity is only slightly influenced by the selection of the material of the protective hose.

Advantages of the Invention

The basic idea of the invention is to use a material that demonstrates almost uniformly high reflection properties over a wavelength bandwidth from 1000 nm to 250 nm as the reflection material for the reflector. Polytetrafluoroethylene demonstrates these properties.

A preferred solution consists in using polytetrafluoroethylene in an optically pure white grade, as a diffusively reflective coating. Colloquially, this is also called optical PTFE.

The polytetrafluoroethylene consists of a layer of up to 2 mm and has reflection properties of more than 97%, specifically over the bandwidth from 1000 nm to 250 nm. It is preferably white and heat-resistant up to about 250-260° C.; it is non-combustible.

A further significant advantage in the use of polytetrafluoroethylene as the reflection material can be seen in that the material has a heat-insulating effect. This means that the heat generated by the UV lamp, particularly the UV-C source, remains in the protective pipe. This results in a closed environment for the UV lamp, which is almost independent of the outside temperature. This makes it possible to use the UV lamp also in areas in which it has not been stable until now and has reacted with temperature sensitivity. The effect consists, among other things, in that the emitted power is far below standard. In this manner, the UV source can now be used also in a cold temperature environment, or one with an alternating temperature, so that a broad application spectrum occurs, with great power efficiency.

Because of the placement of the reflection material and thereby the configuration as a reflector, the result is achieved that a reflector can be additionally introduced, with an aluminum body that is easy to produce, which reflector guides at least part of the emitted rays of the UV source in the direction of a viewing window provided in the protective pipe. The viewing window extends in the longitudinal direction, over part of the mantle surface of the protective pipe. This reflector can have a high degree of reflection in that it is disposed rotationally around the encasing pipe (the material can be formed in this manner and does not have to be configured in facet-like manner), and consists of a material that possesses a high degree of reflection.

A further advantage when using polytetrafluoroethylene lies in that it can be affixed very close to the UV lamp, because it very precisely follows the cylindrical shape of the encasing pipe. The gap between the encasing pipe and the reflector is small, as a result. This additionally increases the reflection power. Furthermore, an additional heat effect occurs, which is beneficial with regard to the emitted power.

It is provided, as a further advantageous embodiment, that at least the region of the viewing window is covered by a transparent material. Because this viewing window or any other aperture opening, as well, offers a possibility for influences from the environment, such as temperature, dirt, etc. to nevertheless penetrate into the protective pipe, but also the temperature in the protective pipe, which is advantageously constant, cannot be maintained, it is provided to dispose a transparent polytetrafluoroethylene hose over the entire encasing pipe, part of which hose covers the viewing window. Since polytetrafluoroethylene has a very low index of refraction, the deflection or also reflection of the UV radiation that exits from the viewing window and is emitted through the hose is very slight. The hose therefore encases the entire protective pipe and ends in the threaded region at the sides, in each instance. Because this hose is also tear-resistant, unintentional "breaking into" the viewing window cannot take place.

If, in spite of this, the encasing pipe or the UV source itself proves to be defective and breaks, no splinters will get outside of the protective pipe, since the hose encloses the protective pipe, including the region of the viewing window. Therefore use in highly sensitive areas, for example in foods production, is also possible.

The hose over the protective pipe can simply be drawn over it in the manner of a bag, and heat-shrunk onto it, so that close contact with the protective pipe is achieved, without liquid or moisture, for example, being able to get between the inner side of the hose and the outer side of the protective pipe.

Alternatively, a transparent plastic hose with a corresponding tear resistance can also be drawn on and heat-shrunk on.

A lens can also be set in front of the viewing window, by means of the formation of a hose, so that the emitted rays are focused or can be output from the viewing window in diffuse manner.

Surprisingly, it has been found that specifically by means of the closed mantling of the UV source, the radiation power is good, independent of the environment, and specifically, the opposite effect is utilized, namely that of keeping the heat generated by the radiation source within the protective pipe. Since a Teflon material is used as the reflector, which material has a high degree of reflection, overheating of the UV source is nevertheless prevented. Therefore the interplay between protective pipe, reflector, and also hose is decisive for the operation of a stable UV source.

Further advantageous embodiments can be derived from the following description, the claims, and the drawings.

DRAWINGS

Figure 2:
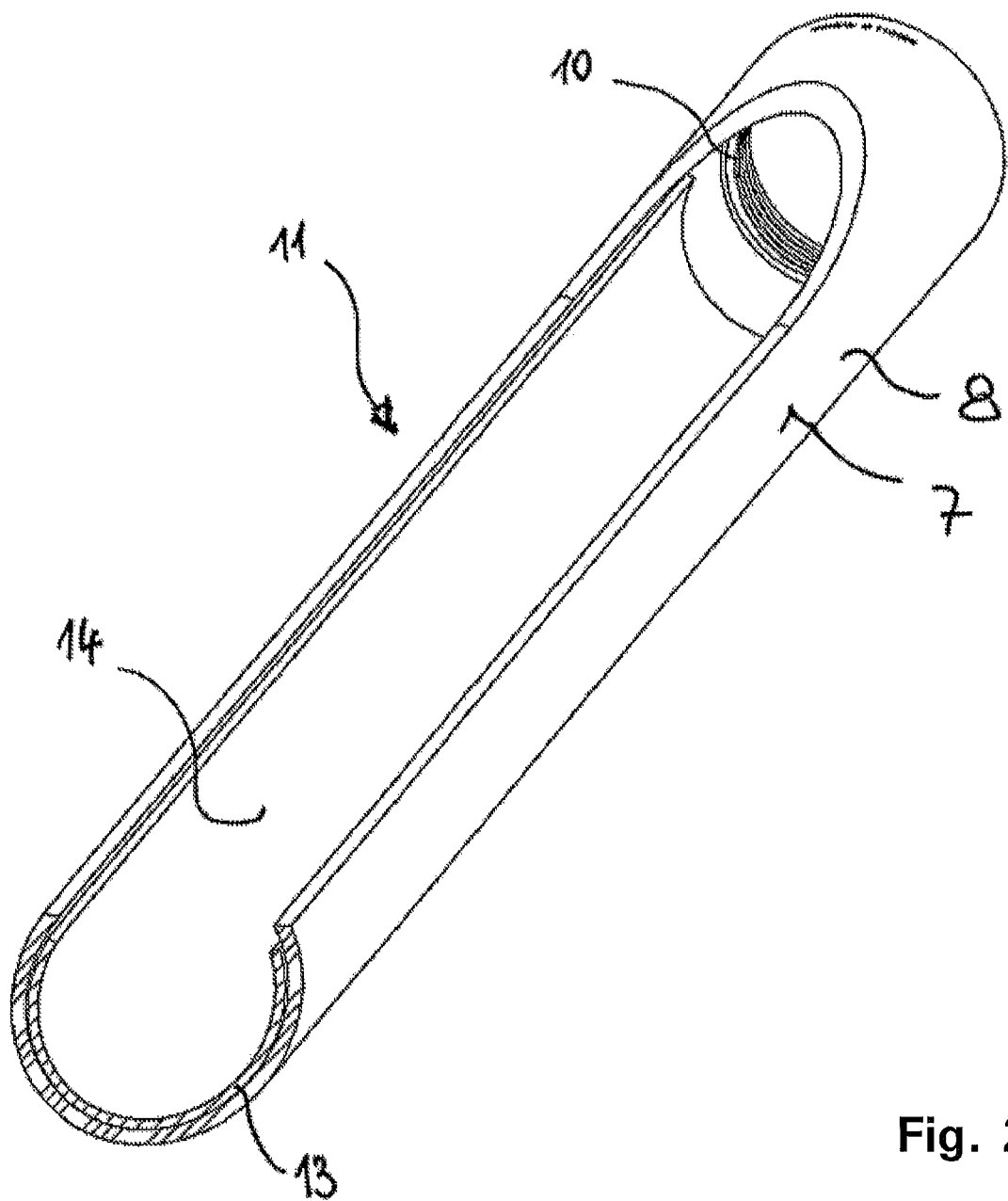
Figure 3:
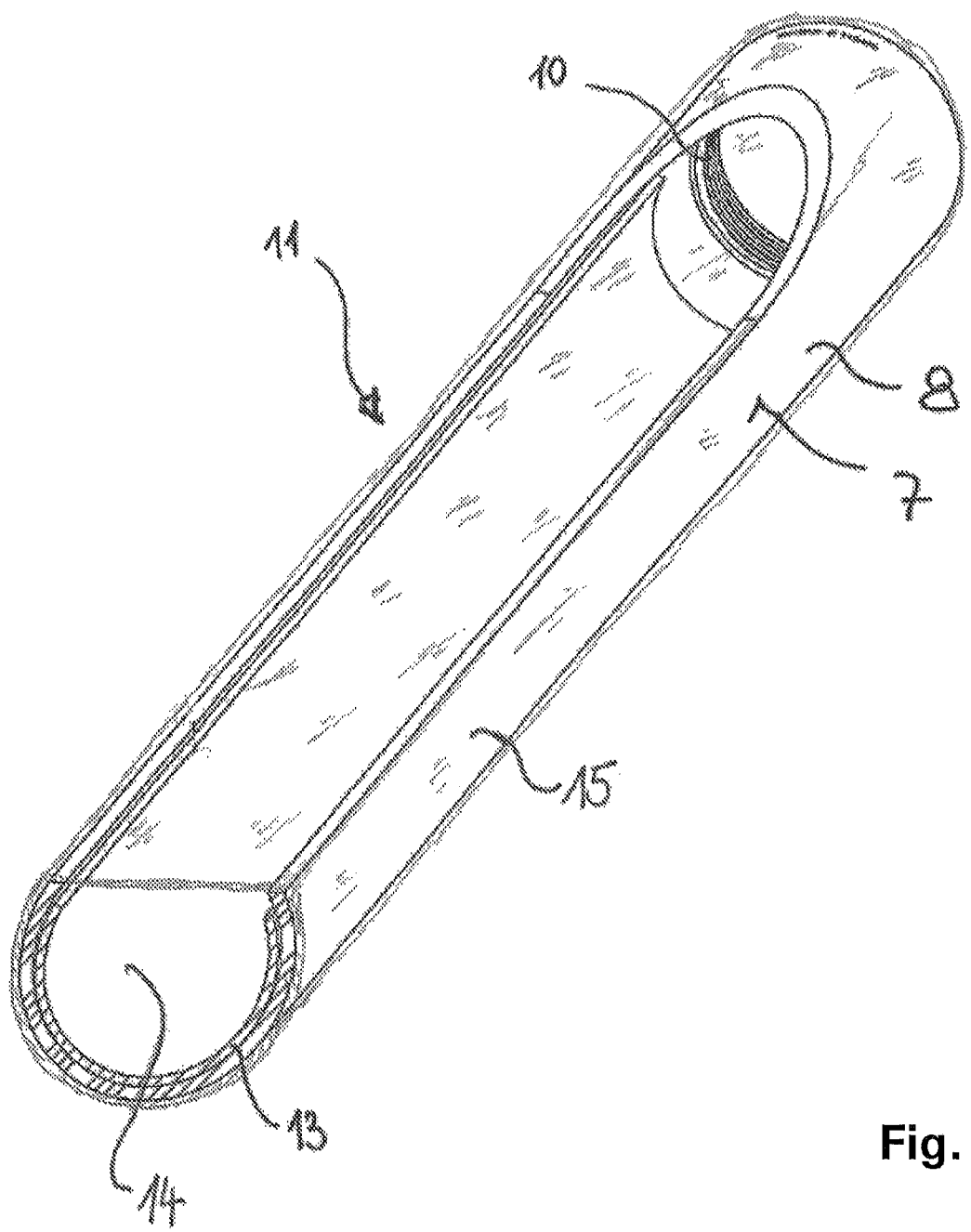

The drawing shows:

FIG. 1 a perspective view of the UV lamp with protective pipe, as an example, in an exploded representation;

FIG. 2 a perspective view of the protective pipe according to the invention;

FIG. 3 a perspective view of the protective pipe, as well as a hose that surrounds the protective pipe, partly in section.

DESCRIPTION OF AN EXEMPLARY EMBODIMENT

In FIG. 1, a UV lamp 1 is shown. This UV lamp 1 consists of a UV tube 2, which in turn comprises a socket 3 with an electrical connector 4. A UV source is coupled with the socket 3; the source is not shown in any detail in the drawing. The UV source is surrounded by a rod-shaped encasing pipe 5. The encasing pipe 5 generally consists of a quartz glass. The end of the UV tube 2 that lies opposite the socket 3 has an end element 6. A protective pipe 8 having a circumferential surface 7 surrounds the encasing pipe 5. The protective pipe 8 has rotation symmetry and is open at both its end faces. In this way, it is possible to push the protective pipe 8 over the encasing pipe 5. In a preferred exemplary embodiment, which is shown in FIG. 1, the protective pipe 8 has elements 9 on both sides, which each interact with inside threads 10 within the protective pipe 8, so that the UV tube 2 can be firmly positioned within the protective pipe 8. Alternative attachment means for the elements 9 are also conceivable, such as, for example, a magnetic closure, bayonet closure, etc.

The protective pipe 8—as also shown in FIG. 2—furthermore has a viewing window 11. This viewing window 11 extends over a partial region of the circumferential surface 7 of the protective pipe 8. This viewing window 11 gives access to the encasing pipe 5 and has no transparent covering. This brings with it the advantage that the radiation 12 of the UV source, which is emitted out of the encasing pipe 5, is released in the direction shown.

The coating 13 of polytetrafluoroethylene is affixed within the protective pipe 8 and forms a reflector 14. A major portion (approximately 95%) of the radiation emitted from the protective pipe 8 is reflected into the environment by way of the reflector. Because of the very simple processing of polytetrafluoroethylene, the reflector 14 can be shaped to fit the encasing pipe 5. Furthermore, very close contact with the encasing pipe 5 is possible, because a facet-like configuration, as it is known when using aluminum, is eliminated.

In FIG. 3, a perspective view of the protective pipe 8 according to FIG. 2 is shown, but with the difference that this pipe is surrounded by a protective hose 15. This protective hose 15, as it is shown in FIG. 3, surrounds the protective pipe 8 completely and lies closely against its circumferential surface 7. This protective hose 15 extends over the free ends of the protective pipe 8, and is accommodated by the elements 9, together with the corresponding seals. The seals lie closely against the outer wall of the protective hose 15. In this way, the encasing pipe 5 that lies on the inside is completely sealed off. If the UV source is exposed to extreme environmental conditions, dirt also cannot get to the encasing pipe from the outside, since the viewing window 11 is completely covered by the hose 15, which consists of transparent material. The material is selected in such a manner that the emitted radiation 12 is not influenced or is only influenced slightly. Preferably, a transparent Teflon material is proposed, since this is also extremely tear-resistant.

In this way, a protective pipe 8 having a reflector 14 as well as a hose 15 that surrounds the protective pipe 8 is made available, which pipe provides uniform UV radiation quality and power almost independent of the field of use, with reference to the environment, because it was surprisingly found that a constant local environment for the radiation source has a significant influence on the emitted radiation power. Furthermore, such a UV source can also be used in critical areas, for example the foods industry.

REFERENCE SYMBOL LIST

Protective Pipe for a UV Tube, Particularly a UV-C Tube
1 UV lamp
2 tube
3 socket
4 connector
5 encasing pipe
6 end element
7 circumferential surface
8 protective pipe
9 elements
10 inside thread
11 viewing window
12 radiation
13 coating
14 reflector
15 hose

The invention claimed is:

1. A protective tube for a UV lamp for accommodating a light-emitting device on having a rod-shaped casing tube,
   wherein the light-emitting device emits UVC radiation,
   wherein the protective tube comprises a circumferential surface and a window extending over a partial region only of the circumferential surface,
   wherein radiation emitted by the rod-shaped casing tube can emerge through the window,
   wherein a coating composed of polytetrafluoroethylene is applied as a reflector to the inner side of the protective tube,
   wherein the protective tube comprises metal, and
   wherein the window is surrounded by a hose that comprises plastic and is at least partially transparent, at least in a region of the window, the hose lying directly against the entire circumferential surface of the protective tube.

2. The protective tube according to claim 1, wherein the protective tube comprises stainless steel or aluminum.

3. The protective tube according to claim 1, wherein the hose comprises polytetrafluoroethylene.

* * * * *